(12) United States Patent
Syrovy et al.

(10) Patent No.: US 12,306,129 B2
(45) Date of Patent: May 20, 2025

(54) SYSTEM FOR MEASURING TEMPERATURE AND MOISTURE OF AIR AND SOIL WITH WIRELESS DATA TRANSMISSION AND METHOD OF ITS PRODUCTION

(71) Applicants: UNIVERZITA PARDUBICE, Pardubice (CZ); ZÁPADOČESKÁ UNIVERZITA V PLZNI, Plzen (CZ); VÝZKUMNÝÚSTAV ROSTLINNÉ VÝROBY, V.V.I., Prague (CZ); CENTRUM ORGANICKÉ CHEMIE S.R.O., Rybitvi (CZ)

(72) Inventors: Tomás Syrovy, Mostek (CZ); Silvan Pretl, Plzen (CZ); Robert Vik, Mesto Touskov (CZ); Jirí Cengery, Zinkovy (CZ); Aleš Hamácek, Chotesov (CZ); Ladislav Mensík, Boskovice (CZ); Lubomír Kubác, Rybitvi (CZ)

(73) Assignees: UNIVERZITA PARDUBICE, Pardubice (CZ); ZÁPADOCESKÁ UNIVERZITA V PLZNI, Plzen (CZ); VÝZKUMNÝÚSTAV ROSTLINNÉ VÝROBY, V.V.I., Prague (CZ); CENTRUM ORGANICKÉ CHEMIE S.R.O., Rybitvi (CZ)

( * ) Notice: Subject to any disclaimer, the term of this patent is extended or adjusted under 35 U.S.C. 154(b) by 145 days.

(21) Appl. No.: 18/022,180

(22) PCT Filed: Aug. 17, 2021

(86) PCT No.: PCT/CZ2021/050086
§ 371 (c)(1),
(2) Date: Feb. 20, 2023

(87) PCT Pub. No.: WO2022/037731
PCT Pub. Date: Feb. 24, 2022

(65) Prior Publication Data
US 2023/0296548 A1     Sep. 21, 2023

(30) Foreign Application Priority Data

Aug. 20, 2020 (CZ) .................. CZPUV 2020-37898
Aug. 20, 2020 (CZ) ......................... CZPV 2020-464

(51) Int. Cl.
*G01N 27/22* (2006.01)
*G01K 1/024* (2021.01)
*G01K 7/16* (2006.01)

(52) U.S. Cl.
CPC ........... *G01N 27/228* (2013.01); *G01K 1/024* (2013.01); *G01K 7/16* (2013.01); *G01N 27/223* (2013.01)

(58) Field of Classification Search
CPC .... G01N 27/228; G01N 27/223; G01K 1/024; G01K 7/16
See application file for complete search history.

(56) References Cited

U.S. PATENT DOCUMENTS 3,968,428 A     7/1976 Numoto
2006/0290360 A1     12/2006 Lee
(Continued)

FOREIGN PATENT DOCUMENTS

CZ     304369 B6     4/2014
EP     2131160 A2     12/2009
(Continued)

*Primary Examiner* — Eman A Alkafawi
*Assistant Examiner* — Suresh K Rajaputra
(74) *Attorney, Agent, or Firm* — Rivka Friedman

(57) ABSTRACT

A system (1) for measuring temperature and moisture of air and soil (3) with wireless data transmission, comprising at least one body (2) which is made of a biodegradable cellulose-based material. The body (2) has an underground part (8) and an above-ground part (9), at least one capacitive soil moisture sensor (4) of the soil (3), at least one resistance soil temperature sensor (5) and conductive paths (10) leading to the capacitive soil moisture sensor (4) and the (Continued)

resistance soil temperature sensor (5) are printed on the surface of the underground part (8) by printing technology. At least one bus (11) for data transmission is printed by means of printing technique on the surface of the above-ground part (9), to which the control unit (6), the radio communication module (7) with the antenna (12) and at least one digital air temperature and relative humidity sensor (13) are removably connected.

15 Claims, 7 Drawing Sheets

(56) References Cited

U.S. PATENT DOCUMENTS

| | | |
|---|---|---|
| 2010/0277185 A1 | 11/2010 | Hughes |
| 2011/0187393 A1 | 8/2011 | Vokey et al. |
| 2014/0025300 A1 | 1/2014 | Okumura |
| 2017/0045487 A1* | 2/2017 | Bauer-Reich ........ H04B 7/1851 |
| 2019/0271656 A1 | 9/2019 | Pruessner |
| 2020/0008299 A1* | 1/2020 | Tran ..................... H05K 1/0386 |
| 2020/0096474 A1* | 3/2020 | Mansergh ............ G01N 27/414 |
| 2022/0003744 A1* | 1/2022 | Kameoka ............. G01N 27/223 |
| 2023/0304959 A1* | 9/2023 | Miller ................ G01N 27/3335 |

FOREIGN PATENT DOCUMENTS

| | | |
|---|---|---|
| WO | 2004109238 A1 | 12/2004 |
| WO | 2014113460 A1 | 7/2014 |
| WO | 2020111922 A1 | 6/2020 |

* cited by examiner

SYSTEM FOR MEASURING TEMPERATURE AND MOISTURE OF AIR AND SOIL WITH WIRELESS DATA TRANSMISSION AND METHOD OF ITS PRODUCTION

FIELD OF THE INVENTION

The invention relates to the field of temperature and moisture detection, in particular to a system and method of its production, which is intended for measuring the temperature and moisture of air and soil with wireless data transmission, used primarily in agriculture, forestry, horticulture and plant cultivation.

BACKGROUND OF THE INVENTION

Sensors are known which detect soil moisture formed on support platforms or base bodies, on which electrodes are arranged which react to changes in the soil depending on the presence of moisture, by changing the electrical resistance, capacity, current or voltage. Sensors detecting soil temperature at various depths are also known, mostly using electric soil thermometers. The base bodies are usually made of a rigid substrate, in particular plastic, which is adapted in shape for potential placement in the soil. Devices using such bodies with electrodes are described, for example, in documents US 20060290360, U.S. Pat. No. 3,968,428, US 201000277185 or US 20140025300. The bodies are usually shaped so that they can be easily embedded in the soil and are equipped with a moisture or temperature sensor. Document US 20190271656 further describes a wireless unit for sensing soil moisture, which transmits measured data from sensors by means of a radio frequency communication unit.

Another known solution is a sensor that measures the temperature and moisture in the soil according to US 20110187393, which is formed as an adhesive foil with two electrodes applied to the upper layer of a hydrophobic substrate covered by a protective layer. The underside of the hydrophobic substrate is provided with an adhesive layer ensuring adhesion to various materials. Due to the growing ecological interest in most industries, there is also a growing interest in creating a more environmentally friendly alternative to soil moisture detection, namely a sensor or system for measuring temperature, soil moisture and microclimate parameters. The solution from the above document solves the issue of ecology only in part, because the body can be made of biodegradable material, but the sensor foil is not, so it is necessary to solve the subsequent environmentally friendly disposal of the sensor. Another disadvantage of this solution is that the sensor is designed as a multilayer structure, the production of which is relatively complicated, time-consuming and economically disadvantageous.

For this reason, the use of common natural biodegradable material is encouraged as the basic body of the detection device, which can be left in nature even after the measurement without environmental pollution. In this respect, however, the materials of the sensors themselves must be of such a composition that would allow this capability/possibility. For this purpose, a sensor has been developed which has an overall biodegradable capability not described in the above solutions.

The object of the invention is therefore to develop a probe or system for measuring temperature and moisture of air and soil at the same time enabling wireless data transmission using an appropriate electronic unit, which would eliminate the above shortcomings, would be an ecological alternative to known soil sensors, would provide accurate data on soil water content, soil temperature and whose production would be time and economically advantageous.

SUMMARY OF THE INVENTION

According to the present invention, the stated object is solved by means of a system for measuring temperature and moisture of air and soil with wireless data transmission. The system comprises at least one body that can be embedded or installed in the soil, on which at least one soil moisture sensor and at least one soil temperature sensor are arranged. Furthermore, the system comprises a control unit to which both sensors are connected and a radio communication module connected to the control unit.

The essence of the present invention is that the body is made of biodegradable material based on cellulose and is divided into an underground part and an above-ground part, where the division results from being installed in the soil or subsequent final position of the body when measuring the temperature and moisture of air and soil. At least one capacitive soil moisture sensor, at least one resistance soil temperature sensor and conductive paths leading to the capacitive soil moisture sensor and the resistance soil temperature sensor are printed on the surface of the underground part. Capacitive soil moisture sensor, resistance soil temperature sensor and conductive paths are printed by printing technique of the group: screen printing, stencil printing, flexographic printing, pad printing, inkjet printing, aerosol jet printing, micro-dispensing, micro-spraying. At least one bus for data transmission is printed on the surface of the above-ground part, using printing technique of the group: screen printing, stencil printing, flexographic printing, pad printing, inkjet printing, aerosol jet printing, micro-dispensing, micro-spraying. The control unit, the radio communication module with the antenna and at least one digital sensor of air temperature and relative humidity are removably connected to the printed bus. This system provides easy and fast measurement of air and soil temperature and moisture using environmentally friendly, degradable materials.

The body is preferably made of wood selected from the group: spruce, larch, pine, Douglas fir, oak, acacia. Alternatively, the body can be made of paper, specifically corrugated fibreboard or compressed recycled paper. Both environmentally friendly, naturally degradable materials provide a completely innovative and new solution of measuring probe that provides relevant measurement results.

The capacitive soil moisture sensor, the resistance soil temperature sensor and the conductive paths are preferably created as a printing pattern formed from ink formulations based on carbon materials from the group: graphite, graphene, carbon nanotubes, and carbon black. In another preferred embodiment, the capacitive soil moisture sensor, the resistance soil temperature sensor and the conductive paths can be created as a printing pattern formed from ink formulations based on conductive polymers such as polyaniline or PANI, poly (3,4-Ethylenedioxythiophene) or PEDOT, poly (3,4-Ethylenedioxythiophene) polystyrene sulfonate or PEDOT:PSS and polypyrrole or PPy, or from ink formulations based on metallic composites and nanoparticle inks such as silver Ag, copper Cu, nickel Ni, gold Au or platinum Pt.

In a preferred arrangement, the body has a flat surface recess in the surface of the underground part, in which at least one capacitive moisture sensor and at least one resistance temperature sensor are printed. This makes the sensors more protected during installation of the body in the soil against potential mechanical damage.

Preferably, the entire surface of the underground part or at least a part thereof, where the capacitive soil moisture sensor, the resistance soil temperature sensor and the conductive paths are printed, is covered with a protective layer against abrasion and for electrical and barrier insulation to the surroundings.

In a preferred arrangement, the control unit, the radio communication module with the antenna and at least one digital sensor of air temperature and relative humidity are removably connected to the bus by means of flexible contacts.

The underground part of the body preferably has a height from 10 to 100 cm and the above-ground part of the body has a height from 20 to 250 cm. In one preferred embodiment, the underground part of the body is divided into three zones, where the first zone is located within 30 cm below the interface between the underground part of the body and the above-ground part of the body and includes a first printed capacitive soil moisture sensor and a first printed resistance soil temperature sensor. The second zone is located from 30 to 60 cm below the interface and includes a second printed capacitive soil moisture sensor and a second printed resistance soil temperature sensor. The third zone is located from 60 to 90 cm below the interface and includes a third printed capacitive soil moisture sensor and a third printed resistance soil temperature sensor.

In a preferred embodiment, the above-ground part of the body is divided into two zones, where the first zone is arranged within 30 cm above the interface and includes a control unit and a first digital air temperature and relative humidity sensor and the second zone is arranged from 30 to 60 cm above the interface and includes a second digital air temperature and relative humidity sensor and a radio communication module with an antenna.

The body is preferably pretreated where the printing layers are printed with at least one technique of the group: grinding, planing, milling, drilling, painting, immersion penetration, spraying, printing.

The printing layers of the above-ground part and the printing layers of the underground part preferably have a distance gap between the conductive paths of the underground part and the bus of the above-ground part.

The invention also relates to a method of producing a system for measuring the temperature and moisture of air and soil with wireless data transmission described above. The core of the present invention is to print on the surface of the underground part of the body made of biodegradable cellulose-based material at least one capacitive soil moisture sensor, at least one resistance soil temperature sensor, conductive paths leading to the capacitive soil moisture sensor and the resistance soil temperature sensor, and at the same time, in the same step, at least one bus for data transmission is printed on the surface of the above-ground part. Printing is performed by printing techniques of the group: screen printing, stencil printing, flexographic printing, pad printing, inkjet printing, aerosol jet printing, micro-dispensing, micro-spraying. The surface of the body is preferably pretreated before printing with at least one technique of the group: grinding, planing, milling, drilling, painting, immersion penetration, spraying, printing. Furthermore, the body with the printed capacitive soil moisture sensor, the resistance soil temperature sensor, the conductive paths and the bus is covered with a protective layer against abrasion and for electrical and barrier insulation to the surroundings.

The advantages of the system and method of its production for measuring temperature and moisture of air and soil according to the invention are in particular that, at the same time, it enables wireless data transmission by means of an appropriate electronic unit, represents an ecological alternative to known soil sensors, provides accurate data on soil water content, soil temperature and its production is also time and economically advantageous.

EXPLANATION OF DRAWINGS

The present invention will be explained in detail by means of the following figures where.

EXAMPLE OF THE INVENTION EMBODIMENTS

Example 1

Figure 1:
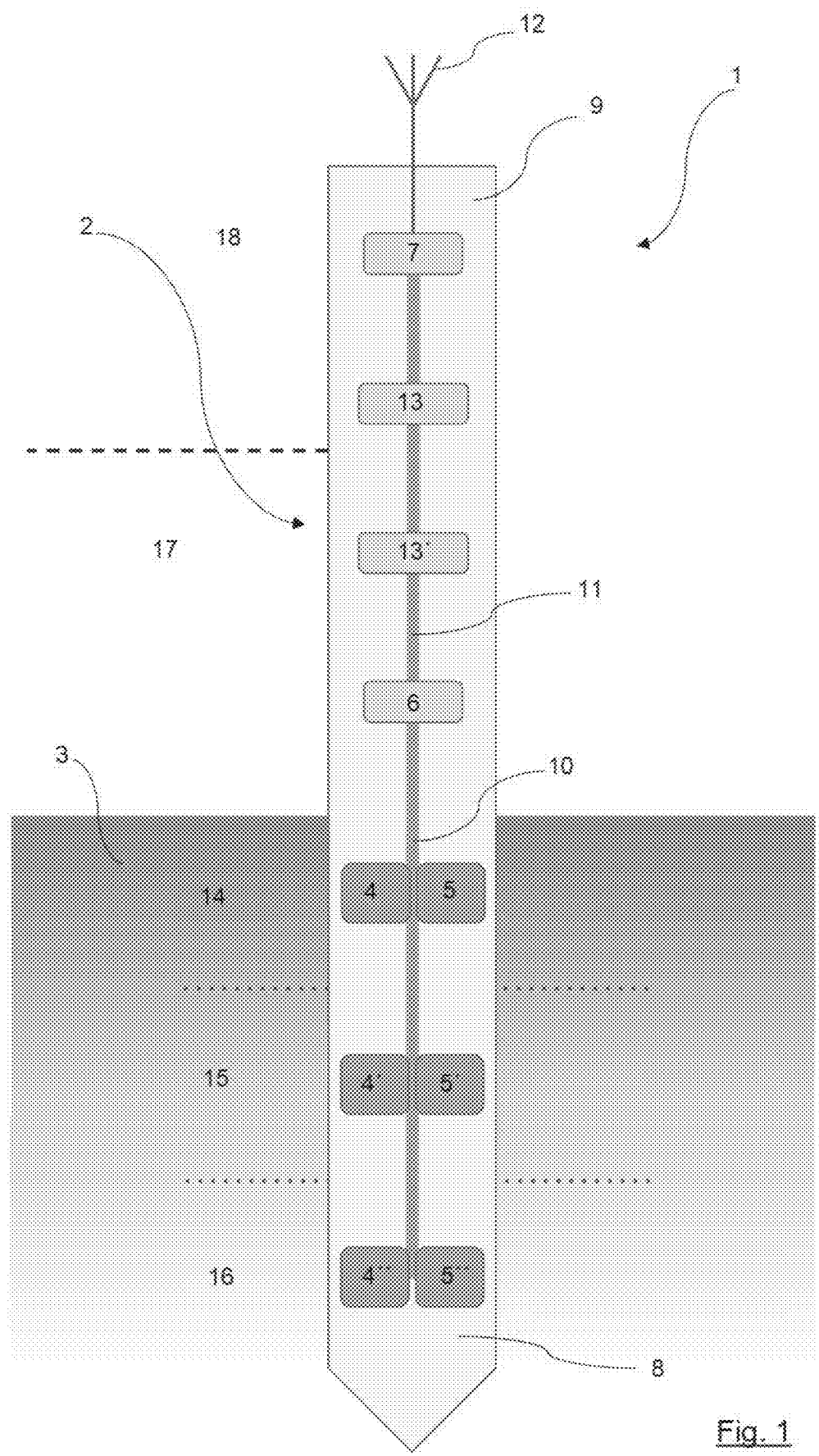
FIG. 1 shows a view of a system for measuring the temperature and moisture of air and soil.
Figure 2:
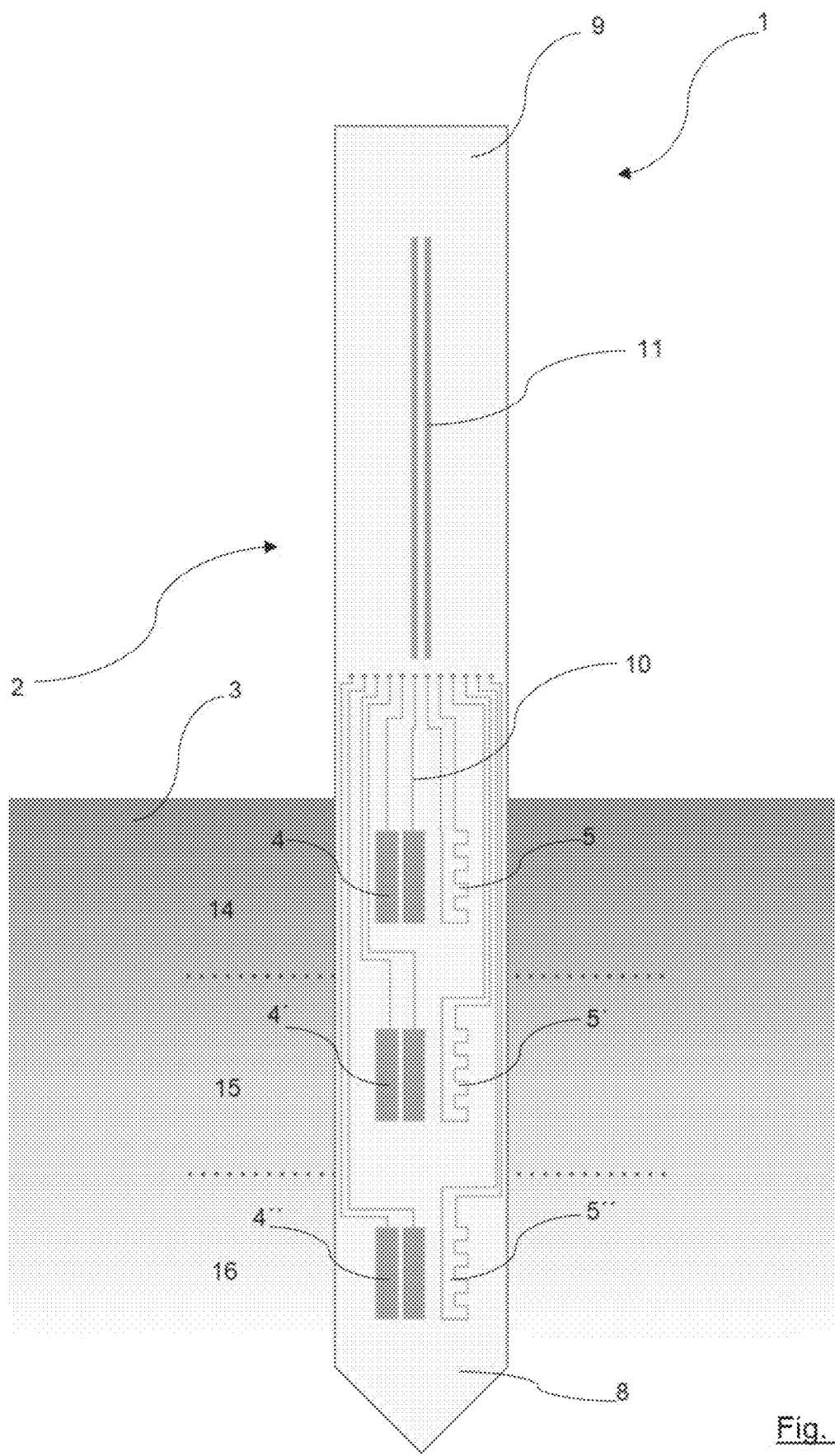
FIG. 2 shows a view of the printing layers on the body.
Figure 3:
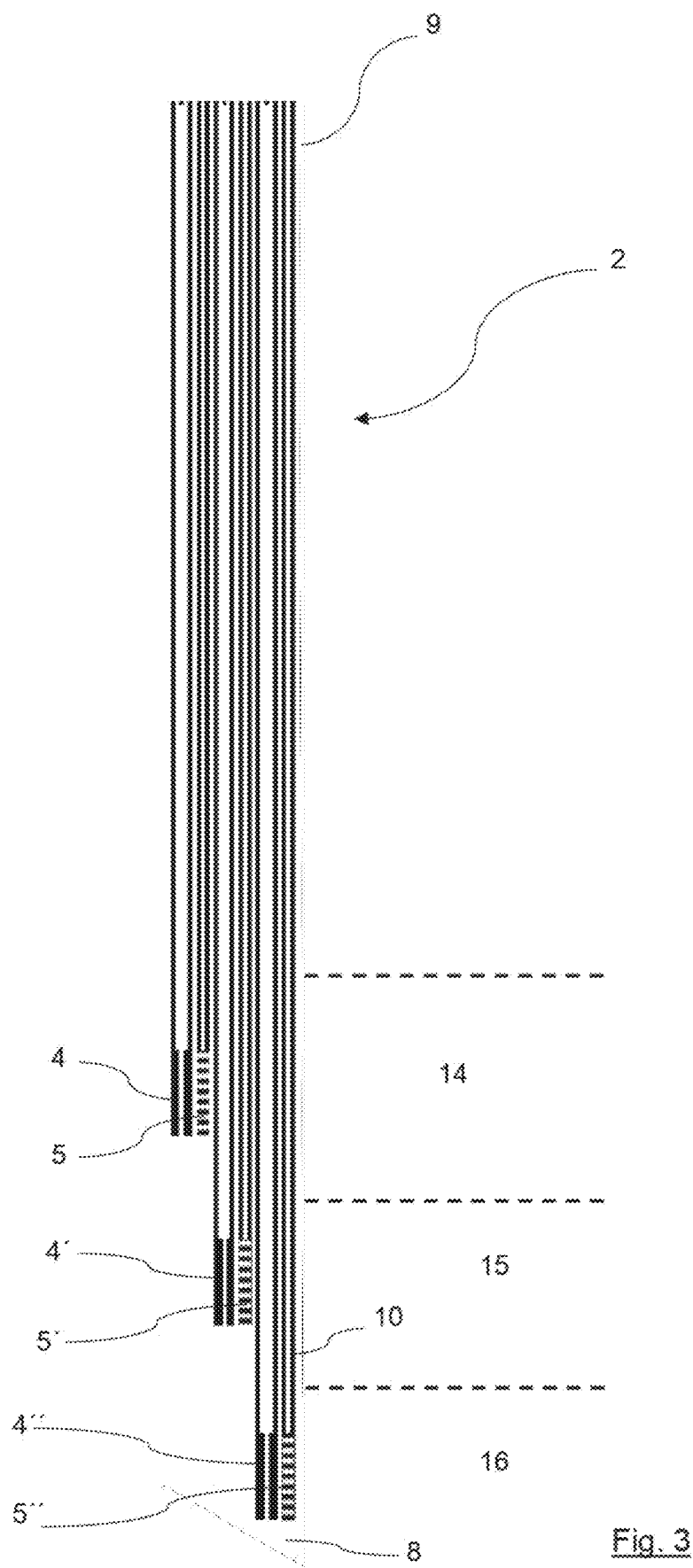
FIG. 3 shows a view of a wood-based body with sensors and conductive paths.

A prism with a width of 146 mm, a thickness of 18.5 mm and a length of 170 cm was prepared from dried spruce wood, with a planed surface provided with a protective water-resistant transparent varnish over the entire surface. One end of the prism was made to the tip by an oblique cut at an angle of 45°, facilitating later installation, i.e. pushing into the soil 3. The wooden prism prepared in this way formed the basic supporting body 2 of the soil probe or system 1 for measuring the temperature and moisture of air and soil 3. As shown in FIG. 1, the whole body 2 was formed by two imaginary parts: the underground part 8 intended for installation in the soil 3 in the length of 60 cm from the bevelled tip in the direction of the longitudinal axis of the body 2 and the directly connecting above-ground part 9 in the remaining length of 110 cm. One of the front sides of the body 2 with a width of 146 mm was chosen as the surface for printing the sensor elements, i.e. the capacitive soil moisture sensor 4 of the soil 3 and the resistance soil temperature sensor 5 of the soil 3 and the connecting conductive paths 10. The printing pattern of the capacitive soil moisture sensor 4 of the soil 3, resistance soil temperature sensor 5 of the soil 3 and connecting conductive paths 10 was formed in the underground part 8 by three zones 14, 15, 16 in the direction of the longitudinal axis of the prism: the first zone 16 in the length of 20 cm from the bevelled tip of the body 2, the second zone 15 and the third zone 14 directly connected to the second zone again in the length of 20 cm. In each zone 14, 15, 16, the printing pattern always contained a pair of sensor elements arranged side by side in the direction of the transverse axis of the body 2, i.e. a capacitive soil moisture sensor 4, 4', 4" of the soil 3 and a resistance soil temperature sensor 5, 5', 5" of the soil 3, as shown in FIG. 2 and FIG. 3.

The capacitive soil moisture sensor 4 of the soil 3 was formed by a pair of rectangular conductive surfaces with a length of 100 mm and a width of 10 mm arranged in parallel next to each other at a distance of 5 mm. The resistance soil temperature sensor 5 of the soil 3 was formed by a conductive path 10 of meander shape with a width of 400 µm, a length of 2000 mm printed in an area of 100 mm×15 mm. The conductive path 10 was printed from a carbon material with a temperature coefficient of electrical resistance TKR=1500 ppm/° C. The printing of all structures, i.e. the capacitive soil moisture sensor 4 of the soil 3, the resistance soil temperature sensor 5 of the soil 3 and the conductive paths 10, was realized by means of a screen printing technique using a stencil with a screen printing fabric of 55 threads per cm. A graphite-based paste was used as the printing ink formulation. The printing was carried out in two passes in wet-on-dry mode with intermediate drying under an IR dryer. The resulting print was dried at 120° C. for 15 minutes. The entire printing pattern of the underground part 8, with the exception of the contact surfaces, was subsequently overprinted by screen-printing using a non-conductive printing ink formulation based on cellulose acetate, in two passes with intermediate drying. A stencil with a screen printing fabric of 55 threads per cm was used for printing and the print was dried at 100° C. for 15 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 were led from the individual sensor elements to the above-ground part 9 of the body 2 at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the control unit 6 then rests on these pads. By means of this control unit 6, the electrical capacity of the capacitive soil moisture sensor 4 of the soil 3 and the electrical resistance of the resistance soil temperature sensor 5 were measured. The control unit 6 further comprises a power supply for the whole system 1 and a digital air temperature and relative humidity sensor 13 for measuring the temperature and relative humidity of air or the microclimate of plants.

In the direction of the longitudinal axis of the above-ground part 9 other conductive paths of a bus 11 were printed with a width of 5 mm terminated 5 mm in front of the end edge of the body 2 used for connecting the radio communication module 7 with the antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 2

Figure 4:
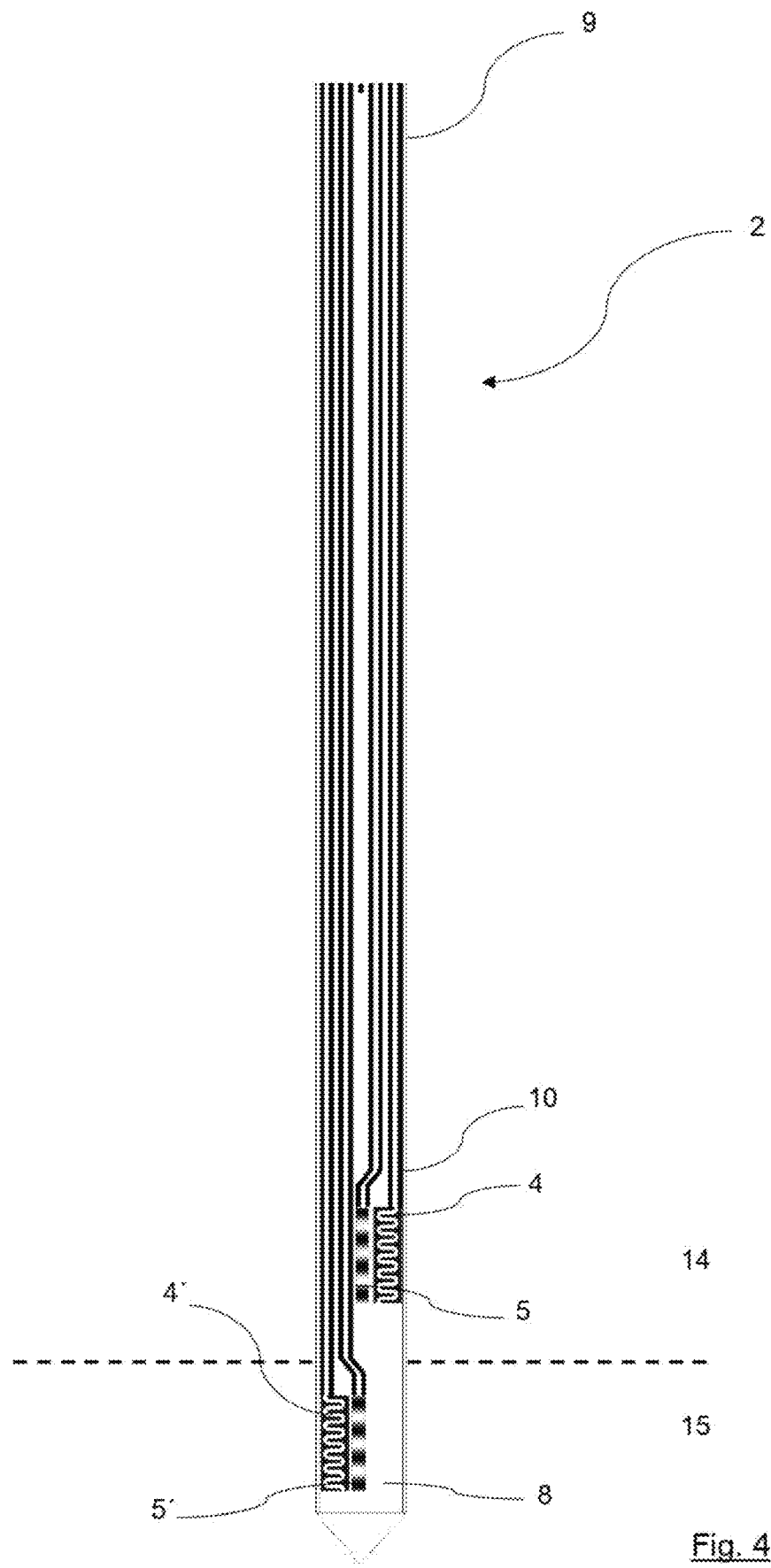
FIG. 4 shows a view of a wood-based body with sensors and conductive paths.

A prism with a width of 95 mm, a thickness of 19 mm and a length of 170 cm was prepared from dried larch wood, with a planed surface provided with a protective water-resistant cellulose-nitrate-based transparent varnish over the entire surface. As shown in FIG. 4, the end of the prism was made to the centred tip by oblique cuts at an angle of 45°, facilitating later installation, i.e. pushing into the soil 3. The wooden prism prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 120 cm. One of the front sides of the body 2 with a width of 95 mm was chosen as the surface for printing the sensor elements, i.e. the capacitive soil moisture sensor 4 of the soil 3 and the resistance soil temperature sensor 5 of the soil 3 and the connecting conductive paths 10. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3, as shown in FIG. 4.

The capacitive soil moisture sensor 4 of the soil 3 consisted of an IDE structure with comb electrodes with a height of 100 mm and a width of 30 mm, where the whole structure had dimensions of 100×40 mm. The resistance soil temperature sensor 5 of the soil 3 was formed by a conductive path 10 of meander shape with a width of 400 µm, a length of 6000 mm printed in an area of 120 mm×30 mm. The conductive path 10 was printed from a carbon material with a temperature coefficient of electrical resistance TKR=1200 ppm/° C. The printing of all structures, i.e. the capacitive soil moisture sensor 4 of the soil 3, the resistance soil temperature sensor 5 of the soil 3 and the conductive paths 10, was realized by means of a screen printing technique using a stencil with a screen printing fabric of 43 threads per cm. A carbon formulation based on graphene particles was used as the printing ink formulation. The printing was carried out in two passes in wet-on-dry mode with intermediate drying under an IR dryer. The resulting print was dried at 120° C. for 20 minutes. The entire printing pattern of the underground part 8, with the exception of the contact surfaces, was overprinted by screen-printing using a printing ink formulation based on polyurethane, in two passes with intermediate drying. A stencil with a screen printing fabric of 77 threads per cm was used for printing and the print was dried at 110° C. for 20 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 are led from the individual sensor elements to the above-ground part 9 of the body 2 at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the non-illustrated control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a non-illustrated digital air temperature and relative humidity sensor 13 for measuring the temperature and relative humidity of air or the microclimate of plants.

In the direction of the longitudinal axis of the above-ground part 9 other conductive paths of a non-illustrated bus 11 were printed with a width of 5 mm terminated 5 mm in front of the end edge of the body 2 used for connecting the non-illustrated radio communication module 7 to the non-illustrated antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 3

Figure 5:
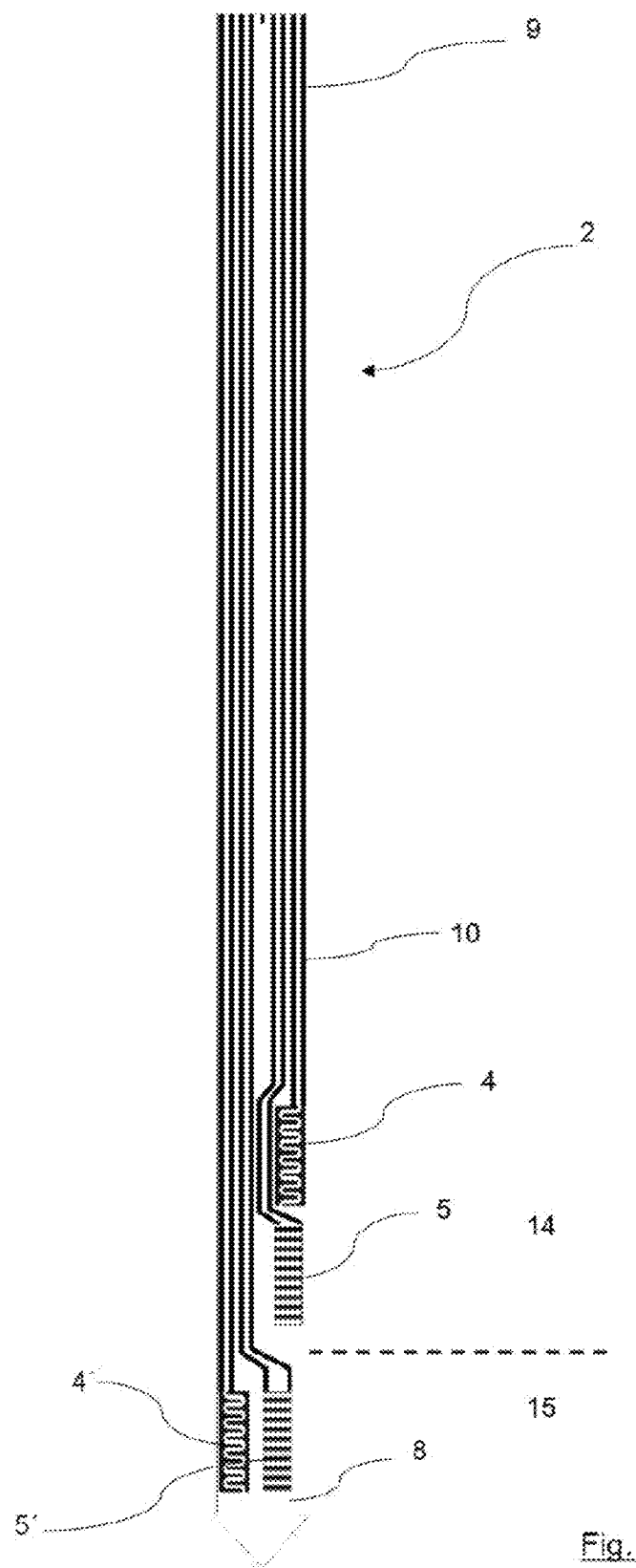
FIG. 5 shows a view of a wood-based body with sensors and conductive paths.

A prism with a width of 95 mm, a thickness of 19 mm and a length of 170 cm was prepared from dried pine wood, with a planed surface provided with a protective water-resistant cellulose-nitrate-based transparent varnish over the entire surface. As shown in FIG. 5, the end of the prism was made to the centred tip by oblique cuts at an angle of 45°, facilitating later installation, i.e. pushing into the soil 3. The wooden prism prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 120 cm. One of the front sides of the body 2 with a width of 95 mm was chosen as the surface for printing the sensor elements, i.e. the capacitive soil moisture sensor 4 of the soil 3 and the resistance soil temperature sensor 5 of the soil 3 and the connecting conductive paths 10. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a length of 100 mm and a width of 30 mm, where the whole structure had dimensions of 100×40 mm. The resistance soil temperature sensor 5 of the soil 3 was formed by a conductive path 10 of meander shape with a width of 400 µm, a length of 4500 mm printed in an area of 120 mm×30 mm. The conductive path 10 was printed from a carbon material with a temperature coefficient of electrical resistance TKR=1500 ppm/°C. The printing of all structures, i.e. the capacitive soil moisture sensor 4 of the soil 3, the resistance soil temperature sensor 5 of the soil 3 and the conductive paths 10, was realized by means of a screen printing technique using a stencil with a screen printing fabric of 55 threads per cm. A graphite-based paste was used as the printing ink formulation. The printing was carried out in two passes in wet-on-dry mode with intermediate drying under an IR dryer. The resulting print was dried at 120° C. for 15 minutes. The entire printing pattern of the underground part 8, with the exception of the contact surfaces, was subsequently over-printed by screen-printing using a non-conductive printing ink formulation based on cellulose acetate, in two passes with intermediate drying. A stencil with a screen printing fabric of 77 threads per cm was used for printing and the print was dried at 100° C. for 15 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 are led from the individual sensor elements to the above-ground part 9 of the body 2 at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the non-illustrated control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a non-illustrated digital air temperature and relative humidity sensor 13 for measuring the temperature and relative humidity of air or the microclimate of plants.

In the direction of the longitudinal axis of the above-ground part 9 other conductive paths of a non-illustrated bus 11 were printed with a width of 5 mm terminated 5 mm in front of the end edge of the body 2 used for connecting the non-illustrated radio communication module 7 with the non-illustrated antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 4

Figure 6:
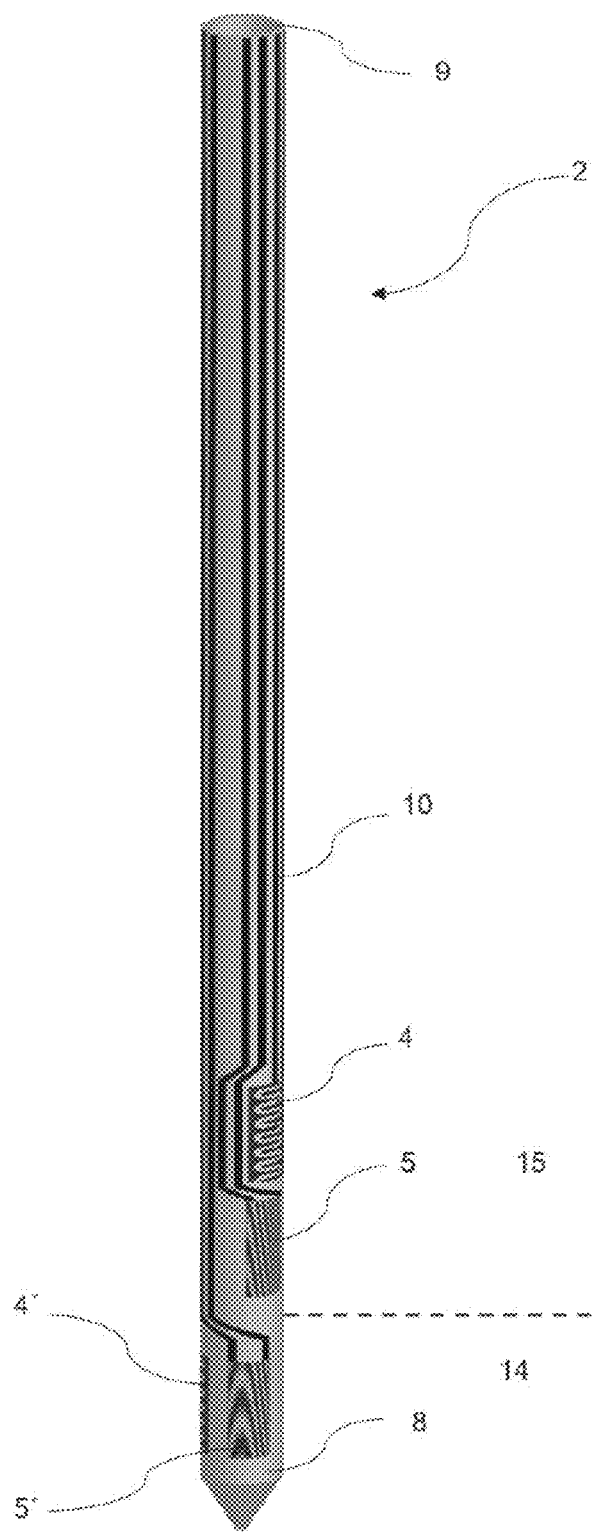
FIG. 6 shows a view of a paper-based body with sensors and conductive paths.

A thick-walled paper tube with a diameter of 50 mm, a length of 160 cm and a wall thickness of 4 mm was used. The paper tube was provided with a cover layer by immersion in cellulose acetate varnish. The given probe based on paper tube requires creating an installation hole using a pole with a diameter of about 50 mm before installation in the ground. The end of the tube was cut into a tip at an angle of 60° to facilitate later installation when pushing into the soil 3, as shown in FIG. 6. The tubular profile prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 110 cm. Because it was a cylindrical object, the printing pattern was realized on the circumference of the tube, when the expanded printing pattern had a width of about 110 mm. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the tube. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e.

a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a height of 100 mm and a width of 30 mm, where the whole structure had dimensions of 100×40 mm. The resistance soil temperature sensor 5 of the soil 3 was formed by a conductive path 10 of meander shape with a width of 600 μm, a length of 2000 mm printed in an area of 120 mm×20 mm. The conductive path 10 was printed from a carbon material with a temperature coefficient of electrical resistance TKR=1200 ppm/° C. The printing of all structures, i.e. the capacitive soil moisture sensor 4 of the soil 3, the resistance soil temperature sensor 5 of the soil 3 and the conductive paths 10, was realized by means of a screen printing technique using a stencil with a screen printing fabric of 55 threads per cm. A graphene particle-based paste was used as the printing ink formulation. The printing was performed on a screen printing machine enabling printing on rotating cylindrical objects. The printing pattern was divided longitudinally into two zones of about 76 cm and the printing was realized in one pass. The resulting print was dried at 120° C. for 20 minutes. The entire printing pattern of the underground part 8, with the exception of the contact surfaces, was overcoated by spraying using a polyurethane-based ink formulation. The varnish was dried at 110° C. for 20 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 are led from the individual sensor elements to the above-ground part 9 of the body 2 at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the non-illustrated control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a non-illustrated digital air temperature and relative humidity sensor 13 for measuring the temperature and relative humidity of air or the microclimate of plants.

In the direction of the longitudinal axis of the above-ground part 9 other conductive paths of a non-illustrated bus 11 were printed with a width of 5 mm terminated 5 mm in front of the end edge of the body 2 used for connecting the non-illustrated radio communication module 7 with the non-illustrated antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 5

A thick-walled paper tube with a diameter of 50 mm, a length of 160 cm and a wall thickness of 4 mm was used. The paper tube was provided with a cover layer by immersion in polyurethane (PUR) varnish. The given probe based on paper tube requires to create an installation hole with a pole with a diameter of about 50 mm before installation in the ground. The end of the tube was cut into a tip at an angle of 60° to facilitate later installation when pushing into the soil 3, similarly as shown in FIG. 6. The tubular profile prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 110 cm. Because it was a cylindrical object, the printing pattern was realized on the circumference of the tube, when the expanded printing pattern had a width of about 110 mm. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a height of 100 mm and a width of 30 mm, where the whole structure had dimensions of 100×40 mm. The resistance soil temperature sensor 5 of the soil 3 was formed by a conductive path 10 of meander shape with a width of 500 μm, a length of 2500 mm printed in an area of 100 mm×25 mm. The conductive path 10 was printed from a carbon material with a temperature coefficient of electrical resistance TKR=1200 ppm/° C. The printing of all structures, i.e. the capacitive soil moisture sensor 4 of the soil 3, the resistance soil temperature sensor 5 of the soil 3 and the conductive paths 10, was realized by means of a micro-dispensing technique using a nozzle with a diameter of 350 μm, pressure of 300 kPa and printing speed of 1200 mm/minute. For printing, 3D data had to be created with respect to the shape of the tube, where, on one side of the tube, data were created for resistance soil temperature sensors 5, 5' of the soil 3 and conductive paths 10 up to the top of the tube and, on the opposite side, there were capacitive soil moisture sensors 4, 4' of the soil 3 and conductive paths 10 to the top of the tube. A graphene-based paste was used as the printing ink formulation. The printing was performed in one pass on each half of the tube, dried and then printed on the other half. The resulting print was dried at 120° C. for 30 minutes. The entire printing pattern of the sensor, with the exception of the contact surfaces, was over-coated by immersion using a PUR-based ink formulation and the coating was dried at 100° C. for 15 minutes.

The printing pattern in the underground part 8 included, together with the sensor elements, connecting conductive paths 10 with a width of 8 mm ensuring the signal transmission to the control unit 6 located in the above-ground part 9 of the body 2. For this purpose, the conductive paths 10 are led from the individual sensor elements to the above-ground part 9 of the body at a distance or at a height of 10 cm from the dividing plane, i.e. the boundary.

The conductive paths 10 were terminated by contact pads with dimensions of 5 mm×5 mm arranged side by side with a spacing of 10 mm on the front side of the body 2.

An array of flexible contact elements of the control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a digital air temperature and relative humidity sensor 13 for measuring the temperature and relative humidity of air or the microclimate of plants.

In the direction of the longitudinal axis of the above-ground part 9 other conductive paths of a bus 11 were printed with a width of 5 mm terminated 5 mm in front of the end edge of the body 2 used for connecting the radio communication module 7 with the antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 6

Figure 7:
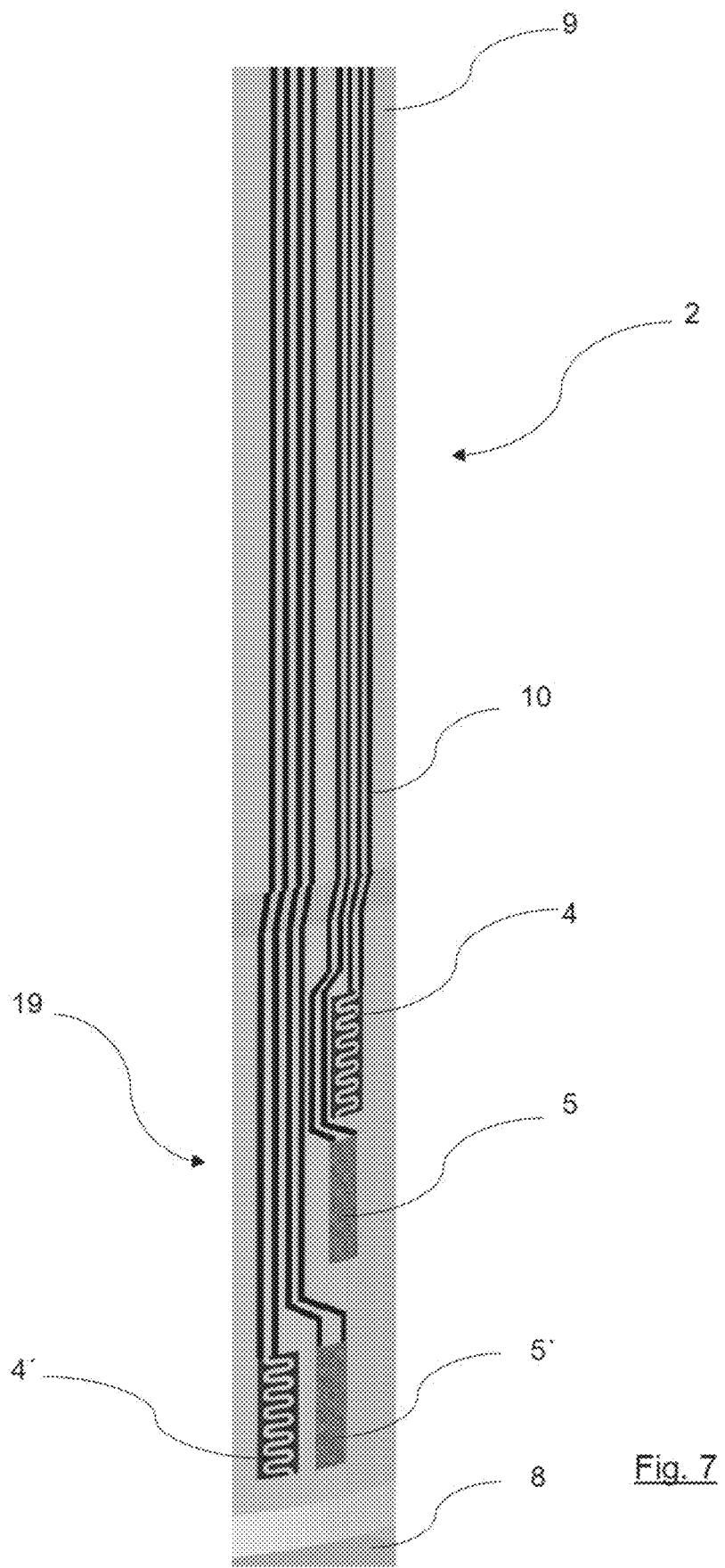
FIG. 7 shows a view of a recess in a paper-based body with sensors and conductive paths.

A prism with a width of 96 mm, a thickness of 18.5 mm and a length of 170 cm was prepared from dried spruce wood, with a planed surface provided with a protective water-resistant cellulose-nitrate-based transparent varnish over the entire surface. The end of the prism was made to the centred tip by oblique cuts at an angle of 45°, facilitating later installation, i.e. pushing into the soil 3. The wooden prism prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 120 cm. One of the front sides of the body 2 with a width of 96 mm was chosen as the surface for printing the sensor elements, i.e. the capacitive soil moisture sensor 4 of the soil 3 and the resistance soil temperature sensor 5 of the soil 3 and the connecting conductive paths 10. The underground part 8 of the prism was milled by 3 mm with a milling cutter in the zone of 20 mm above the tip and 20 mm below the end of the underground part 8 against the plane of the given side of the prism to form a recess 19, with a leading edge at an angle of 45°, as shown in FIG. 7. This makes the sensor elements more protected during installation of the body 2 in the soil 3 against potential mechanical damage. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a height of 100 mm and a width of 30 mm, where the whole structure had dimensions of 100×40 mm. The resistance soil temperature sensor 5 of the soil 3 was formed by a conductive path 10 of meander shape with a width of 800 µm, a length of 1875 mm printed in an area of 120 mm×25 mm. The conductive path 10 was printed from a carbon material with a temperature coefficient of electrical resistance TKR=1700 ppm/° C. The printing of all structures, i.e. the capacitive soil moisture sensor 4 of the soil 3, the resistance soil temperature sensor 5 of the soil 3 and the conductive paths 10, was realized by means of an inkjet technique using XAAR print heads and a resolution of 360 dpi. The print head was 1 mm above the highest point of the prism. A globule nanoparticle-based ink formulation with SWCNT in a ratio of 100:1 was used as the printing ink formulation. The printing was performed in two passes in wet-on-wet mode. The resulting print was dried at 120° C. for 15 minutes. The entire printing pattern of the system 1, with the exception of the contact surfaces, was over-coated by spraying applied using a cellulose acetate-based ink formulation and the coating was dried at 100° C. for 20 minutes.

The printing pattern in the underground part 8 included, together with the sensor elements, connecting conductive paths 10 with a width of 8 mm ensuring the signal transmission to the control unit 6 located in the above-ground part 9 of the body 2. For this purpose, the conductive paths 10 are led from the individual sensor elements to the above-ground part 9 of the body at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the non-illustrated control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a non-illustrated digital air temperature and relative humidity sensor 13 for measuring the temperature and relative humidity of air or the microclimate of plants.

In the direction of the longitudinal axis of the above-ground part 9 other conductive paths of a non-illustrated bus 11 with a width of 5 mm terminated 5 mm in front of the end edge of the body 2 used for connecting the non-illustrated radio communication module 7 with the non-illustrated antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 7

A prism with a width of 95 mm, a thickness of 19 mm and a length of 150 cm was prepared from dried larch wood, with a planed surface provided with a protective water-resistant cellulose-nitrate-based transparent varnish over the entire surface. The end of the prism was made to the centred tip by oblique cuts at an angle of 45°, facilitating later installation, i.e. pushing into the soil 3. The wooden prism prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 100 cm. One of the front sides of the body 2 with a width of 95 mm was chosen as the surface for printing the sensor elements, i.e. the capacitive soil moisture sensor 4 of the soil 3 and the resistance soil temperature sensor 5 of the soil 3 and the connecting conductive paths 10. The underground part 8 of the prism was milled by 3 mm with a milling cutter in the zone of 20 mm above the tip and 20 mm below the end of the underground part 8 against the plane of the given side of the prism to form a recess 19, with a leading edge at an angle of 45°, as shown in FIG. 7. This makes the sensor elements more protected during installation of the body 2 in the soil 3 against potential mechanical damage.

The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a height of 100 mm and a width of 30 mm, where the whole structure had dimensions of 100×40 mm. The resistance soil temperature sensor 5 of the soil 3 was formed by a conductive path 10 of meander shape with a width of 1500 μm, a length of 1200 mm printed in an area of 120 mm×30 mm. The conductive path 10 was printed from a carbon material with a temperature coefficient of electrical resistance TKR=1700 ppm/° C. The printing of all structures, i.e. the capacitive soil moisture sensor 4 of the soil 3, the resistance soil temperature sensor 5 of the soil 3 and the conductive paths 10, was realized by means of a micro-spraying technique using a nozzle with a diameter of 150 μm, pressure of 400 kPa and printing speed of 1200 mm/minute. For printing, 3D data had to be created with respect to the nature of the milled surface and to ensure the nozzles are always at the same distance, i.e. 1 mm above the surface from the highest point of the prism. A globule nanoparticle-based ink formulation with SWCNT in a ratio of 100:1 was used as the printing ink formulation. The resulting print was dried at 120° C. for 30 minutes. The entire printing pattern of the sensor, with the exception of the contact surfaces, was over-coated by spraying using a PUR-based ink formulation and the coating was dried at 100° C. for 15 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 are led from the individual sensor elements to the above-ground part 9 of the body at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the non-illustrated control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a non-illustrated digital air temperature and relative humidity sensor 13 for measuring the temperature and relative humidity of air or the microclimate of plants.

In the direction of the longitudinal axis of the above-ground part 9 other conductive paths of a non-illustrated bus 11 were printed with a width of 5 mm terminated 5 mm in front of the end edge of the body 2 used for connecting the non-illustrated radio communication module 7 with the non-illustrated antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 8

A thick-walled paper substrate with dimensions with a width of 100 mm, a thickness of 10 mm and a length of 160 cm was created from the recycled pulp, which was provided with a layer over the entire surface by spraying a protective water-resistant transparent varnish based on cellulose acetate. The given probe based on paper profile requires creating an installation hole using a metal prism with dimensions of 100×10 mm before installation in the ground. The end of the profile was made to the centred tip by oblique cuts at an angle of 45°, facilitating later installation when pushing into the soil 3. The tubular profile prepared in this way formed the basic supporting body 2 of the soil probe or system 1 for measuring the temperature and moisture of air and soil 3. The whole body 2 was formed by two imaginary parts: the underground part 8 intended for installation in the soil 3 in the length of 50 cm from the bevelled tip in the direction of the longitudinal axis of the body 2 and the directly connecting above-ground part 9 in the remaining length of 110 cm. One of the front sides of the body 2 with a width of 100 mm was chosen as the surface for printing the sensor elements and the conductive paths of the connecting structures. The printing pattern of the capacitive soil moisture sensor 4 of the soil 3, resistance soil temperature sensor 5 of the soil 3 and connecting conductive paths 10 was formed in the underground part 8 by two zones 14, 15 in the direction of the longitudinal axis of the prism. Second zone 15 in the length of 30 cm from the tip of the body 2 and first zone 14 directly connected to the second zone in the length of 20 cm. In each zone 14, 15, the printing pattern always contained a pair of sensor elements arranged side by side in the direction of the transverse axis of the body 2, i.e. a capacitive soil moisture sensor 4, 4' of the soil 3 and a resistance soil temperature sensor 5, 5' of the soil 3.

The capacitive soil moisture sensor 4 of the soil 3 consisted of an IDE structure with comb electrodes with a length of 100 mm and a width of 30 mm, where the whole structure had dimensions of 100×40 mm. The resistance soil temperature sensor 5 of the soil 3 was formed by a conductive path 10 of meander shape with a width of 400 μm, a length of 4500 mm printed in an area of 120 mm×30 mm. The conductive path 10 was printed from a carbon material with a temperature coefficient of electrical resistance TKR=1500 ppm/° C. The printing of all structures, i.e. the capacitive soil moisture sensor 4 of the soil 3, the resistance soil temperature sensor 5 of the soil 3 and the conductive paths 10, was realized by means of a screen printing technique using a stencil with a screen printing fabric of 55 threads per cm. A graphite-based paste was used as the printing ink formulation. The printing was carried out in two passes in wet-on-dry mode with intermediate drying under an IR dryer. The resulting print was dried at 120° C. for 20 minutes. The entire printing pattern of the underground part 8, with the exception of the contact surfaces, was subsequently overprinted by screen-printing using a non-conductive printing ink formulation based on cellulose acetate, in two passes with intermediate drying. A stencil with a screen printing fabric of 77 threads per cm was used for printing and the print was dried at 110° C. for 20 minutes.

The printing pattern in the underground part 8 included, together with the sensor elements, connecting conductive paths 10 with a width of 5 mm ensuring the signal transmission to the control unit 6 located in the above-ground part 9 of the body 2. For this purpose, the conductive paths 10 are led from the individual sensor elements to the above-ground part 9 of the body at a distance or at a height of 10 cm from the dividing plane, i.e. the boundary. The conductive paths 10 were terminated by contact pads with dimensions of 5 mm×5 mm arranged side by side with a spacing of 10 mm on the front side of the body 2.

An array of flexible contact elements of the control unit 6 then rests on these pads. By means of this control unit 6, the electrical capacity of the capacitive soil moisture sensor 4 of the soil 3 and the electrical resistance of the resistance soil temperature sensor 5 of the soil 3 are measured. The control unit 6 further comprises a power supply for the whole system 1 and a digital air temperature and relative humidity sensor 13 for measuring the temperature and relative humidity of air or the microclimate of plants.

In the direction of the longitudinal axis of the above-ground part 9 other conductive paths of a bus 11 were printed with a width of 5 mm terminated 5 mm in front of the end edge of the body 2 used for connecting the radio communication module 7 with the antenna 12 and supplying it with electricity. The radio communication module 7 is located on top of the body 2 and provides the transmission of measured data via the LoRa LPWAN network. The radio communication module 7 includes an electronic circuit for measuring temperature and relative humidity of air.

Example 9

The design of the system 1 is the same as in Example 9, except that a three-layer corrugated fibreboard with a thickness of 15 mm, a width of 100 mm and a length of 150 cm was used as the printing substrate or the body 2.

Example 10

The design of the system 1 is the same as in Example 2, except that a composite based on silver Ag particles, which has a significantly higher conductivity, was used for printing the capacitive soil moisture sensor 4 of the soil 3, the resistance soil temperature sensor 5 of the soil 3, the conductive paths 10 and the bus 11. The conductive paths 10 and the bus 11 were printed in a width of 2 mm.

Example 11

The design of the system 1 is the same as in Example 3, except that a printing ink formulation based on poly (3,4-Ethylenedioxythiophene) polystyrene sulfonate or PEDOT:PSS with a dry matter content of 5.5% wt was used for printing the capacitive soil moisture sensor 4 of the soil 3, the resistance soil temperature sensor 5 of the soil 3, the conductive paths 10 and the bus 11.

Example 12

The design of the system 1 is the same as in Example 3, except that Douglas fir wood was used as the printing substrate or the body 2.

Example 13

The design of the system 1 is the same as in Example 10, except that oak wood was used as the printing substrate or the body 2 and the conductive layers were printed on the basis of nickel Ni paste.

Example 14

The design of the system 1 is the same as in Example 1, except that acacia wood was used as the printing substrate or the body 2.

Example 15

The design of the system 1 is the same as in Example 10, except that flexographic printing with a silver printing ink formulation was used as the printing technique.

Example 16

Embodiment as in Example 7, except that pad printing with a silver printing ink formulation was used as the printing technique.

Example 17

Embodiment as in Example 7, except that aerosol jet printing with a silver printing ink formulation based on silver nanoparticles was used as the printing technique.

Example 18

Embodiment as in Example 10, except that a copper printing ink formulation was used, which was subsequently sintered by means of photonic sintering.

INDUSTRIAL APPLICABILITY

The system for measuring temperature and moisture of air and soil with wireless data transmission and the method of its production can be particularly used in agriculture, horticulture and plant cultivation, i.e. in monitoring and data collection in the above mentioned areas.

LIST OF REFERENCE NUMERALS

1 system
2 body
3 soil
4, 4', 4" capacitive soil moisture sensor
5, 5', 5" resistance soil temperature sensor
6 control unit
7 radio communication module
8 underground part
9 above-ground part
10 conductive path
11 bus
12 antenna
13, 13" digital air temperature and relative humidity sensor
14 first zone of the underground part
15 second zone of the underground part
16 third zone of the underground part
17 first zone of the above-ground part
18 second zone of the above-ground part
19 recess

The invention claimed is:

1. A system for measuring temperature and moisture of air and soil with wireless data transmission, comprising at least one body which can be embedded in the soil, on which at least one soil moisture sensor and at least one soil temperature sensor are arranged; further comprising a control unit to which both sensors are connected and a radio communication module, with an antenna, connected to the control unit, wherein the body is made of a biodegradable cellulose-based material selected from the group consisting of: spruce, larch, pine, Douglas fir, oak, and acacia, has an underground part and an above-ground part, wherein the soil moisture sensor is a capacitive soil moisture sensor, wherein the soil temperature sensor is a resistance soil temperature sensor, wherein the capacitive soil moisture sensor, the resistance soil temperature sensor and conductive paths leading to a capacitive soil moisture sensor and a resistance soil temperature sensor are printed on the surface of the underground part, wherein the capacitive soil moisture sensor, the resistance soil temperature sensor, and the conductive paths are printed by means of a printing technique selected from the group consisting of: screen printing, stencil printing, flexographic printing, pad printing, inkjet printing, aerosol jet printing, micro-dispensing, and micro-spraying; wherein the capacitive soil moisture sensor, the resistance soil temperature sensor, and the conductive paths are created as a printing pattern formed from ink formulations based on carbon materials selected from the group consisting of: graphite, graphene, carbon nanotubes, and carbon black; and at least one bus for data transmission is printed on the surface of the above-ground part by means of a printing technique selected from the group consisting of: screen printing/stencil printing, flexographic printing, pad printing, inkjet printing, aerosol jet printing, micro-dispensing, and micro-spraying, to which the control unit, the radio communication module with the antenna and at least one digital air temperature and relative humidity sensor are removably connected in contact.

2. The system according to claim 1, wherein the body is made of corrugated fibreboard-based paper or compressed recycled paper.

3. The system according to claim 1, wherein the capacitive soil moisture sensor, the resistance soil temperature sensor, and the conductive paths are created as a printing pattern formed from ink formulations based on conductive polymers.

4. The system according to claim 1, wherein the capacitive soil moisture sensor, the resistance soil temperature sensor, and the conductive paths are created as a printing pattern formed from ink formulations based on metallic composites and nanoparticle inks.

5. The system according to claim 1, wherein the body has a flat surface recess in the surface of the underground part, in which at least one capacitive moisture sensor and at least one resistance temperature sensor are printed.

6. The system according to claim 1, wherein the entire surface of the underground part or at least a part thereof, where the capacitive soil moisture sensor, the resistance soil temperature sensor, and the conductive paths are printed, is covered with a protective layer against abrasion and for electrical and barrier insulation to the surroundings.

7. The system according to claim 1, wherein the control unit, the radio communication module with the antenna and at least one digital air temperature and relative humidity sensor are removably connected to the bus by means of flexible contacts.

8. The system according to claim 1, wherein the underground part of the body has a height from 10 to 100 cm and the above-ground part of the body has a height from 20 to 250 cm.

9. The system according to claim 8, wherein the underground part of the body is divided into three zones, where the first zone is located within 30 cm below the interface between the underground part of the body and the above-ground part of the body and includes a first printed capacitive soil moisture sensor and a first printed resistance soil temperature sensor; the second zone is located from 30 to 60 cm below the interface and includes a second printed capacitive soil moisture sensor and a second printed resistance soil temperature sensor, and the third zone is located from 60 to 90 cm below the interface and includes a third printed capacitive soil moisture sensor and a third printed resistance soil temperature sensor-.

10. The system according to claim 8, wherein the above-ground part of the body is divided into two zones, where the first zone is arranged within 30 cm above the interface and includes a control unit and a first digital air temperature and relative humidity sensor and the second zone is arranged from 30 to 60 cm above the interface and includes a second digital air temperature and relative humidity sensor and a radio communication module with an antenna.

11. The system according to claim 1, wherein the body is pretreated where the printing layers are printed with at least one technique selected from of the group consisting of: grinding, planing, milling, drilling, painting, immersion penetration, spraying, and printing.

12. The system according to claim 1, wherein the printing layers of the above-ground part and the printing layers of the underground part have a distance gap between the conductive paths of the underground part and the bus of the above-ground part.

13. A method of producing a system for measuring the temperature and moisture of air and soil with wireless data transmission according to claim 1, wherein on the surface of the underground part of the body made of biodegradable cellulose-based material, at least one capacitive soil moisture sensor, at least one resistance soil temperature sensor, and conductive paths leading to the capacitive soil moisture sensor and the resistance soil temperature sensor are printed, and at the same time, in the same step, at least one bus for data transmission is printed on the surface of the above-ground part, with printing being performed by printing at least one techniques selected from the group consisting of: screen printing, stencil printing, flexographic printing, pad printing, inkjet printing, aerosol jet printing, micro-dispensing, and micro-spraying.

14. The method according to claim 13, wherein the surface of the body is pretreated before printing with at least one technique selected from of the group consisting of: grinding, planing, milling, drilling, painting, immersion penetration, spraying, and printing.

15. The method according to claim 13, wherein the body with the printed capacitive soil moisture sensor, the resistance soil temperature sensor, the conductive paths and the bus are covered with a protective layer against abrasion and for electrical and barrier insulation to the surroundings.

* * * * *